(12) United States Patent
Flexman et al.

(10) Patent No.: US 11,730,931 B2
(45) Date of Patent: Aug. 22, 2023

(54) BALLOON CATHETER COMPRISING SHAPE SENSING OPTICAL FIBERS

(71) Applicant: KONINKLIJKE PHILIPS N.V., Eindhoven (NL)

(72) Inventors: Molly Lara Flexman, Melrose, MA (US); Milan Jan Henri Marell, Eindhoven (NL); Paul Thienphrapa, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1197 days.

(21) Appl. No.: 16/314,996

(22) PCT Filed: Jul. 11, 2017

(86) PCT No.: PCT/EP2017/067312
§ 371 (c)(1),
(2) Date: Jan. 3, 2019

(87) PCT Pub. No.: WO2018/011158
PCT Pub. Date: Jan. 18, 2018

(65) Prior Publication Data
US 2019/0307995 A1  Oct. 10, 2019

Related U.S. Application Data

(60) Provisional application No. 62/362,724, filed on Jul. 15, 2016.

(51) Int. Cl.
*A61M 25/10* (2013.01)
*A61B 34/20* (2016.01)
*G01D 5/353* (2006.01)
*A61B 5/06* (2006.01)
*A61B 5/00* (2006.01)
*A61B 90/00* (2016.01)

(52) U.S. Cl.
CPC ......... *A61M 25/10187* (2013.11); *A61B 5/06* (2013.01); *A61B 5/6853* (2013.01); *A61M 25/104* (2013.01); *G01D 5/35316* (2013.01); *A61B 2034/2061* (2016.02); *A61B 2090/3966* (2016.02)

(58) Field of Classification Search
CPC ................. A61M 25/10187; A61B 2034/2061
See application file for complete search history.

(56) References Cited

U.S. PATENT DOCUMENTS

| | | | |
|---|---|---|---|
| 9,693,707 B2 | 7/2017 | Chan et al. | |
| 2005/0075704 A1* | 4/2005 | Tu | A61N 5/062 977/932 |
| 2008/0077225 A1* | 3/2008 | Carlin | A61B 5/1076 623/1.11 |
| 2009/0000567 A1 | 1/2009 | Hadjioannou et al. | |

(Continued)

*Primary Examiner* — Angela M Hoffa
*Assistant Examiner* — Younhee Choi

(57) ABSTRACT

A sensor device includes a flexible instrument (20) including a lumen (22). A plurality of shape or strain sensing optical fibers (14, 16, 18) is integrated in the flexible instrument in the lumen and extends over a length of the flexible instrument. The plurality of optical fibers is configured to measure movement relative to one another to sense a change in distance between the plurality of optical fibers to detect a state of a reconfigurable portion (24) of the flexible instrument.

18 Claims, 6 Drawing Sheets

(56) References Cited

U.S. PATENT DOCUMENTS

| | | | |
|---|---|---|---|
| 2011/0098533 A1* | 4/2011 | Onoda | G02B 23/2476 |
| | | | 600/117 |
| 2012/0271339 A1 | 10/2012 | O'Beirne et al. | |
| 2013/0211261 A1* | 8/2013 | Wang | G16H 50/30 |
| | | | 600/476 |
| 2013/0310685 A1 | 11/2013 | Chan et al. | |
| 2015/0238275 A1 | 8/2015 | Kung et al. | |
| 2016/0157939 A1 | 6/2016 | Larkin et al. | |
| 2017/0281025 A9* | 10/2017 | Glover | A61F 2/2427 |

* cited by examiner

BALLOON CATHETER COMPRISING SHAPE SENSING OPTICAL FIBERS

CROSS-REFERENCE TO PRIOR APPLICATIONS

This application is the U.S. National Phase application under 35 U.S.C. § 371 of International Application Serial No. PCT/EP2017/067312, filed on Jul. 11, 2017, which claims the benefit of U.S. Patent Application No. 62/362,724, filed on Jul. 15, 2016. This application is hereby incorporated by reference herein.

BACKGROUND

Technical Field

This disclosure relates to optical shape sensing and, more particularly, to devices, systems and methods for optical shape sensing with integration of multiple sensors.

Description of the Related Art

Fiber-Optic RealShape™ (FORS™) uses light along a multicore optical fiber to reconstruct a shape along that fiber. One principle involved makes use of a distributed strain measurement in the optical fiber using characteristic Rayleigh backscatter or controlled grating patterns. The shape along the optical fiber begins at a specific point along the sensor, known as the launch or zero position, and a subsequent shape position and orientation are relative to that point. The optical fiber is typically 200 microns in diameter and can be up to a few meters long while maintaining millimeter level accuracy.

FORS™ fibers can be integrated into a wide range of medical devices to provide live guidance medical procedures. As an example, a guidewire and catheter may be employed for navigation of the heart with the optical shape sensing measurement overlaid upon a pre-operative computed tomography (CT) image.

Balloon angioplasty is a radiation and contrast intensive procedure performed primarily to increase a lumen diameter of a blood vessel which has become partially occluded by plaque or constriction stenosis. The balloon catheter is first navigated to the site of an occlusion. A guidewire is used to cross the occlusion and then the balloon catheter follows. A mixture of saline and contrast agent is injected into the balloon to inflate it, during which time the pressure in the balloon is carefully monitored to avoid rupturing the balloon within the body. The balloon is held in its inflated state (for seconds to minutes) and is re-inflated multiple times to achieve successful reopening.

Following treatment, the balloon is deflated and removed from the body. Fluoroscopy is employed for navigating the guidewire and catheter into the correct position, and also for monitoring the balloon during inflation, pressurization, depressurization, and deflation. The fluoroscopy is used to see the surface contours of the balloon to confirm that it is expanding properly across potentially sharp and tough calcifications and blockages. Fluoroscopy detects balloon rupture. Balloon catheters are also employed for vascular procedures including valvuloplasty, ballooning of endografts to seal them in place, balloon deployment for localized drug delivery to a vessel, stent placement (normal or drug-eluting) to hold the vessel open, etc.

SUMMARY

In accordance with the present principles, a sensor device includes a flexible instrument including a lumen. A plurality of shape or strain sensing optical fibers is integrated in the flexible instrument in the lumen and extends over a length of the flexible instrument. The plurality of optical fibers is configured to measure movement relative to one another to sense a change in distance between the plurality of optical fibers to detect a state of a reconfigurable portion of the flexible instrument.

Another sensor device includes a flexible instrument including at least one lumen. A plurality of shape or strain sensing optical fibers are integrated in the flexible instrument in the at least one lumen and extend over a length of the flexible instrument. The plurality of optical fibers are configured to measure movement relative to one another to sense a change in distance between the plurality of optical fibers to detect a state of a reconfigurable portion of the flexible instrument. The plurality of optical fibers include a principal fiber extending an entire length of the flexible instrument to measure shape or strain changes along the length; and at least one supplemental optical fiber (16, 18) extending the entire length of the flexible instrument and configured to provide shape or strain sensing to measure the reconfigurable portion of the flexible instrument.

A method for sensing flexure in a reconfigurable portion of a flexible instrument includes configuring a plurality of shape or strain sensing optical fibers in a flexible instrument within at least one lumen, the plurality of optical fibers extending a length of the flexible instrument; and measuring movement of the plurality of optical fibers relative to one another to sense a change in distance between the plurality of optical fibers to detect a state of a reconfigurable portion of the flexible instrument.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
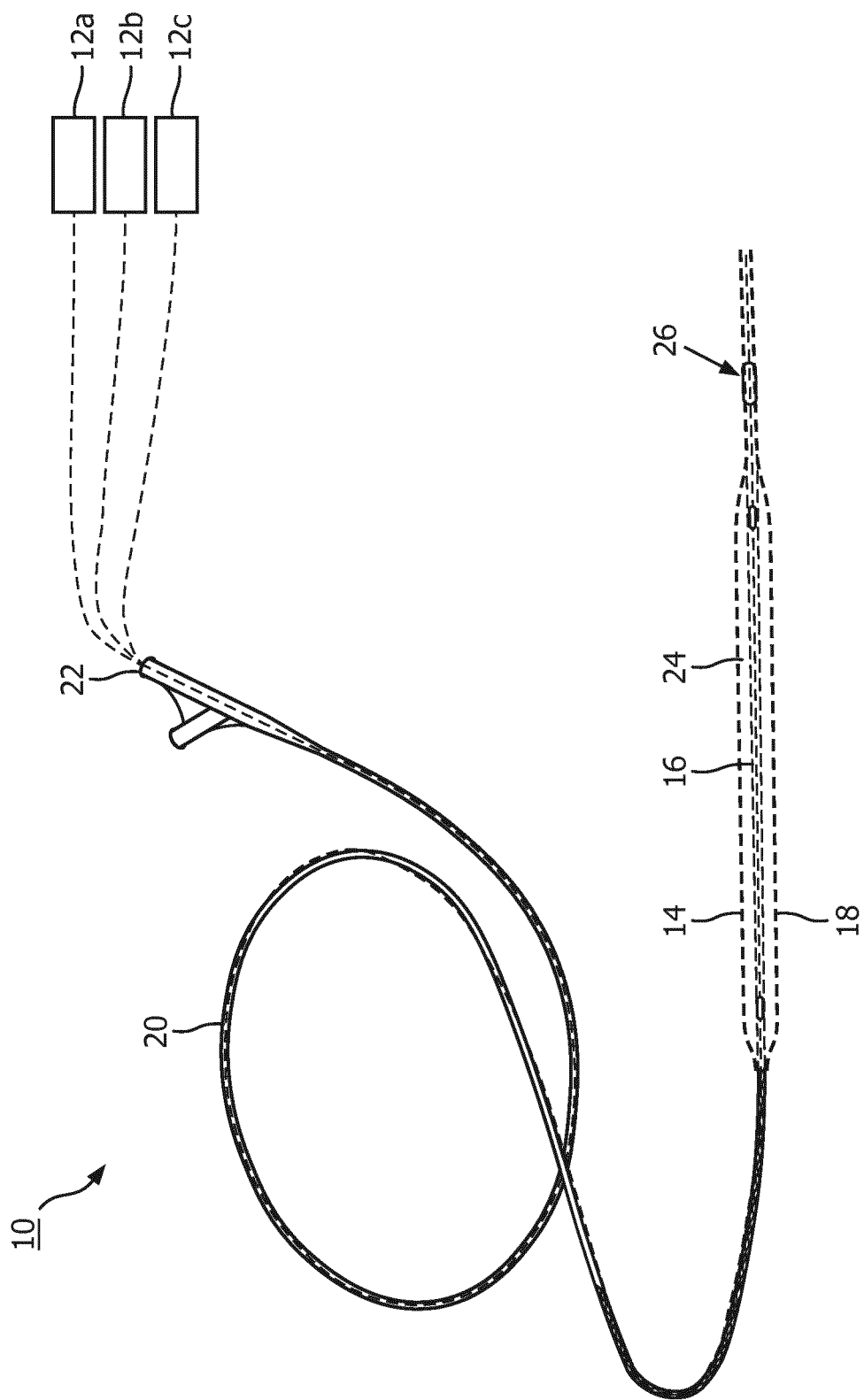
FIG. 1 is a perspective view showing a three optical fiber shape sensing system with the optical fibers integrated into a balloon catheter in accordance with one embodiment.

In accordance with the present principles, multiple optical sensors (e.g., optical fibers) are integrated together for reconstructing a surface of a balloon or other flexible surface or membrane. A balloon catheter is an example of such a device, but the present principles can be applied to any other device such as, e.g., stents, endografts, valves, clips, prosthetics, etc. In one embodiment, all sensors reconstruct their full length from outside a device (e.g., from a fixed launch position) to a tip of the device. In another embodiment, a single fiber reconstructs a full length of the device, while the other fibers reconstruct only a portion of the fiber that covers the balloon or other flexible instrument. The fibers are registered together in a region proximal to the balloon or other flexible instrument.

Balloon catheters and other therapeutic devices (e.g., stents, endografts, clips, etc.) are commonly used in many intravascular procedures. These devices are navigated into position and deployed under fluoroscopy guidance. Optical shape sensing (OSS) or Fiber-Optic RealShape™ (FORS™) can be integrated into the devices to provide 3D shape information along an entire device (including the balloon, graft, etc.) without the need for fluoroscopy. This can reduce exposure to radiation by a patient and operating room staff, and can provide more nuanced 3D information about the device than can be seen via 2D fluoroscopy imaging. Mechanical considerations may make it difficult to sense a 3D device using a single optical shape sensing fiber. Multiple sensors can be integrated into the device and employed together to extrapolate the 3D surface of the device. Using multiple full shape sensing fibers includes significant redundant information along a majority of the device. The present principles provide mechanisms by which supplementary fibers can be simplified or intelligently combined with a primary fiber. This reduces the complexity of a measurement system (and therefore reduces the cost as well).

It should be understood that the present principles will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems and procedures in all areas of the body such as the cardiovascular system, lungs, gastro-intestinal tract, excretory organs, etc. The elements depicted in the FIGS. may be implemented in various combinations of hardware and software and provide functions which may be combined in a single element or multiple elements. The present principles may be employed in mechanical systems, such as plumbing applications, automotive applications, etc.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk—read only memory (CD-ROM), compact disk—read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C).

This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a balloon catheter 10 includes a balloon or balloon portion 24 having a plurality of optical shape sensing fibers 14, 16, 18 disposed thereon. The multiple shape sensing fibers 14, 16, 18 are integrated within the device 10 (including the balloon 24). Integrated within the device 10 may include passed through a lumen and/or permanently affixed as manufactured within the device 10. In one embodiment, the integration of N (wherein N is greater than 1) shape sensing fibers 14, 16, 18 into the device 10 includes threading the fibers into the material of the device 10 and balloon 24 (e.g., into a lumen). The fibers 14, 16, 18 need to include slack in portion 26 to permit for the expansion of the balloon 24, or the slack can be developed from the proximal end portion where the fibers 14, 16 and 18 are loose in a lumen 22 of a catheter portion 20 of the device 10.

In one configuration, there are N>1 fibers 14, 16, 18 that are integrated into the device 10. At the proximal portion of the device 10, each fiber returns back to its own launch position or launch 12a, 12b, 12c (also referred to as 0,0,0). These launches 12a-12c can all be physically located in a same fixture or position in a room. A relationship between the launch positions 12a-12c of the various fibers 14, 16, 18 are registered (e.g., via techniques known in the art, including mechanical registration, shape-to-shape registration, etc.). In the shaft of the catheter 20, each fiber may have its own lumen or they may use a common lumen 22. In the balloon 24, the fibers 14, 16, 18 are distributed across a surface, each within its own or shared lumen or path. The lumens or paths are preferably provided within the walls of the balloon 24.

The entire length of each fiber 14, 16, 18 from launch positions 12a-12c to tip (portion 26) is reconstructed using FORS™, and the shape is therefore known. As a result, there is redundant information along the shaft of the catheter 20. This redundancy can be employed to improve accuracy by taking an average of the fiber positions or taking a weighted average based on a metric of shape confidence (for example, noise on the twist, amount of twist, amount of curvature, etc.).

In another embodiment, the integration of fibers includes one principal shape sensing fiber 14 and N supporting fibers (wherein N is greater than or equal to one). This helps to eliminate a large amount of redundancy in the shape sensing measurement. The length of the catheter 20 may be, e.g., 1-2 m while the balloon length may be about 1 cm to about 4 cm. In the single principal fiber approach, a single shape sensing fiber 14 is employed to sense the entire length of the catheter 20. This single shape sensing fiber 14 has a launch 12a that is in a fixed position in the room. The N supplementary fibers e.g., fibers 16 and 18 run the entire length of the catheter body 20, but only actively shape sense the balloon portion 24. Coordinate systems for the fibers 14, 16, and 18 need to be registered together.

Figure 2:
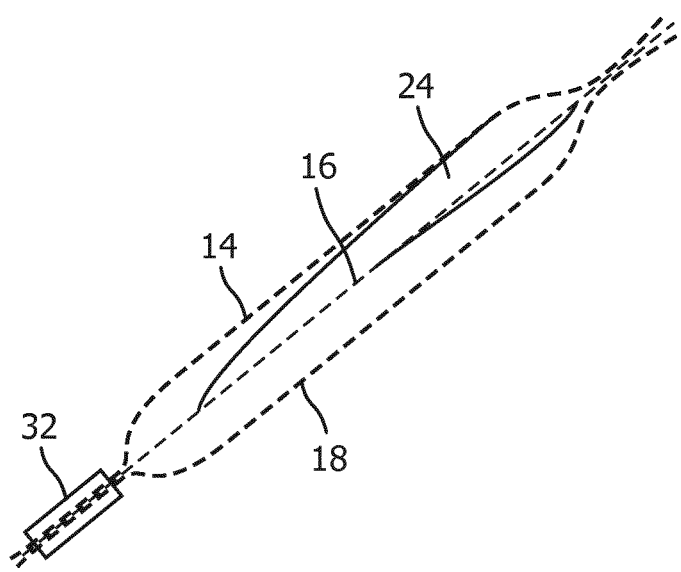
FIG. 2 is a perspective view showing a three optical fiber shape sensing system with a principal fiber and supplemental fibers running along portions of a balloon and having a second launch position in accordance with one embodiment.

Referring to FIG. 2, for the single principal fiber approach, an example of a secondary launch region 32 is employed in the catheter shaft immediately prior to the balloon portion 24. The secondary launch region 32 provides sufficient uniqueness in its optical reflection so that it can be identified accurately within the optical measurement. For example, a fiber transition or geometrical feature at the secondary launch region 32 can provide an accurate identification position. The secondary launch region 32 also provides a known relationship between the N+1 fibers (14, 16, 18) in that region. This may be a mechanically known relationship or a relationship that is calibrated during the manufacturing process or immediately prior to use. Knowing the position of the secondary launch 32, additional or redundant data from the supplemental fibers can be filtered or simply eliminated from the measurement.

In one embodiment, radio-opaque or similar markers for image-based registration may be employed. This may be especially relevant to device designs in which the device is not mechanically coupled to the catheter body (for example, endografts). In such as case, a registration between the supporting fibers (integrated into the endograft) and the primary fiber (integrated into the deployment device shaft) can be performed during an intervention or operation prior to device deployment. In one embodiment, the launch region 32 may include a specific form that is recognizable in an image. This specific form may include a 2D or 3D feature, e.g., straight sections and curved sections. The specific form may be positioned in regions other than the launch region 32.

With the use of the N supplementary fibers that only sense the balloon 24, the fibers may be measured in different ways from the principal fiber. These supplementary fibers have many technical specifications that can simplify their design. For example, the supplemental fibers may be significantly shorter in length and may provide lower (or higher) resolution measurements in some situations. Additional technical implementation may include that the supplemental fibers can be pushed into a measurement frequency range that is outside of the core or principal measurement fiber. All of the fibers may then be measured with a same interrogator (light source) using multiple frequencies/wavelengths of light.

Figure 3:
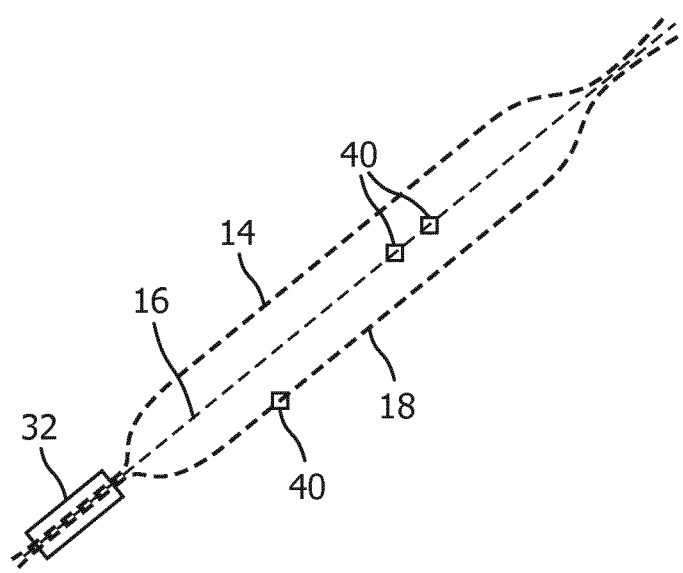
FIG. 3 is a perspective view showing a three optical fiber shape sensing system with a principal fiber and supplemental fibers having fiber Bragg gratings running along portions of a balloon and having a second launch position in accordance with one embodiment.

Referring to FIG. 3, in another embodiment, instead of employing full shape sensing fibers, a single-core fiber-Bragg grating (FBG) based strain sensor 40 may be implemented. While a single FBG does not give shape information on its own, information from the FBG 40 may be combined with knowledge of the mechanical properties of the balloon or other device to provide an approximation of the deformations along the balloon surface.

A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, strain causes a shift in the Bragg wavelength.

One advantage of this technique is that various sensor elements 40 can be distributed over the length of a fiber. Along the length of the fiber, at various positions, a multitude of FBG sensors can be located. In a useful implementation, FBGs 40 are located continuously at positions along the sensor (the FBGs 40 are concatenated). In other implementations, FBGs 40 are located at discrete positions (with less accuracy). From the strain measurement of each FBG 40, the curvature of the structure can be inferred at that position. From the multitude of measured positions, the total three-dimensional form can be determined.

FBGs 40 may also be employed on the supporting fibers that are shifted outside of the wavelength range used by the main fiber 14. By using a lower resolution measurement in the supporting fibers 16, 18, the total wavelength range measured by the system is only increased by a small amount.

A combination of the uses of the FBGs 40 may also be employed. For example, in more complex devices such as endografts, it may be advantageous to employ a hybrid approach (e.g., fibers with and without FBGs). A hybrid approach may include using feedback from FBGs 40 to approximate deformations and to shift wavelengths to enable less data (lower wavelength range). The hybrid approach may also be used to balance among complexity, redundancy, and cost to achieve the desired level of precision.

In other embodiments, the functionality of multiple fibers may be simulated with a single physical fiber via multiplexing signals in time and/or space. In one embodiment, a fiber already traversing the balloon section may be withdrawn from the balloon section, switched to another of N lumens and re-inserted through the balloon in another lumen to trace a shape of a different side of the balloon. This process may be repeated a number of times to obtain shape data through one or more other available lumens. This approach may employ an insertion/retraction mechanism for switching between lumens for the fiber to traverse or may be performed manually. The extent of insertion/retraction needed can be communicated via a visual overlay on a system display, e.g., using shape sensing data. Mechanical actuation by the insertion/retraction mechanism coupled with computerization of the process can be implemented to share the task burden with a practitioner.

Figure 4:
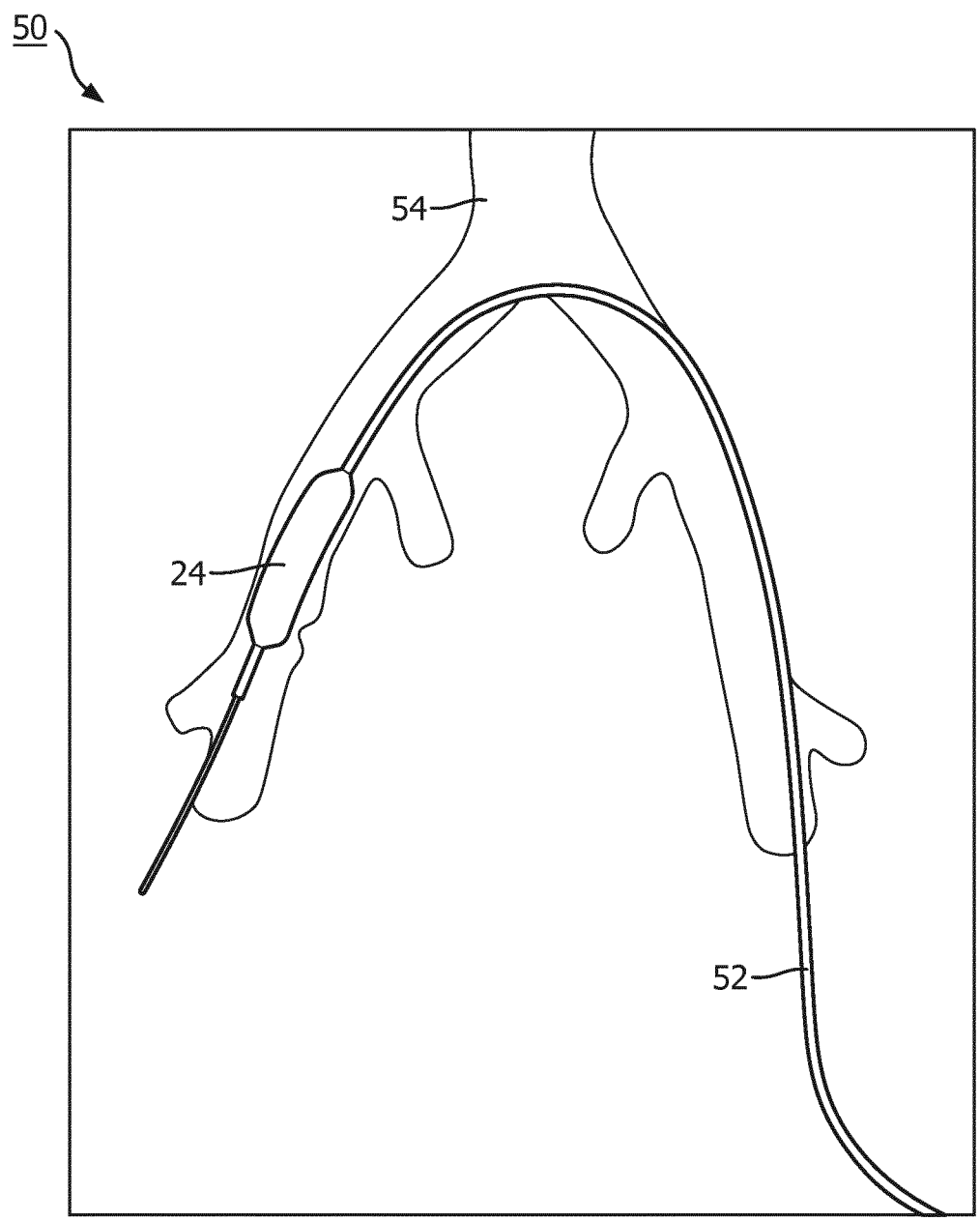
FIG. 4 is an image showing a shape sensing system in a balloon catheter displayed as an overlay on an anatomical image in accordance with one embodiment.

Referring to FIG. 4, in accordance with the present principles, a user can see a 3D representation of the device 24 overlaid on an anatomical model or image 50 of a blood vessel 54. A representation of shape data 52 can be constructed from the sensor measurements, along with additional information provided by the user, from a priori information about the device deployment, material properties, etc., and/or from intraoperative imaging.

Figure 5:
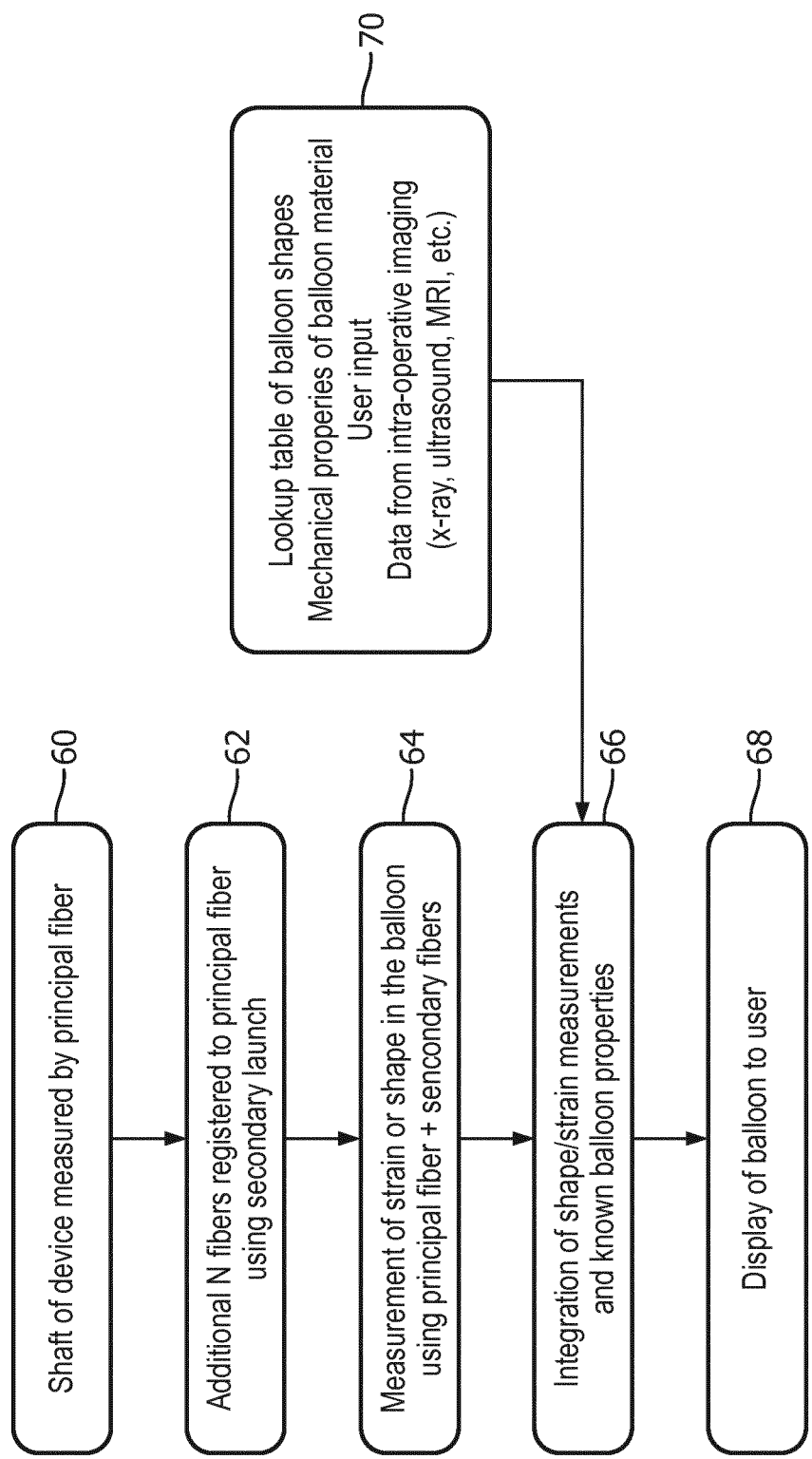
FIG. 5 is a flow diagram showing a method for displaying a device using shape or strain sensing data in accordance with an illustrative embodiment.

Referring to FIG. 5, a flow diagram shows construction of a visual representation of shape data from the sensor measurements in accordance with one illustrative embodiment. In block 60, a principal fiber measures a shape or strain of the device along its entire length. In block 62, additional or supplemental fibers are registered to the principal fiber using a secondary launch. These supplemental fibers capture shape data over less than an entire length of the device and may be employed in specific regions or orientations along a portion of the device. In block 64, measurements (strain or shape) of the device or a specific area of the device are taken using the principal fiber and the supplemental fibers. In one embodiment, the supplemental fibers cover a balloon portion while the principal fiber covers an entire catheter device with the balloon portion.

In block 66, shape/strain measurements are integrated with or modified by known device (e.g., balloon) properties. These properties are input from block 70 and may include information about the dimensions or characteristic of the balloon. For example, a lookup table may be employed with balloon shapes and dimensions at various stages of inflation/deflation. Other information may include mechanical properties of the balloon material, user input, data from intraoperative imaging (x-ray, ultrasound, MRI, etc.).

In block 68, the balloon, its position and state of inflation/deflation can be displayed to a user. The display may include a display device and may include an overlay of shape/strain data on a pre-operative or intra-operative image. The display can be updated, as needed. The display can show data detected from one or each of the FORS™-enabled devices or individual fibers in each device that has more than one shape sensing or strain sensing fiber integrated therein.

It should be understood that the embodiments described may include the use of multiple fibers to sense the surface of the device and apply to Rayleigh scattering (enhanced and regular) as well as other types of scattering, fiber Bragg grating implementations of shape sensing fiber, etc. Embodiments apply to manual and robotic deployment of devices. Although described in the context of balloons, the present principles are applicable to other devices, such as, e.g., endografts, valves, etc.

Figure 6:
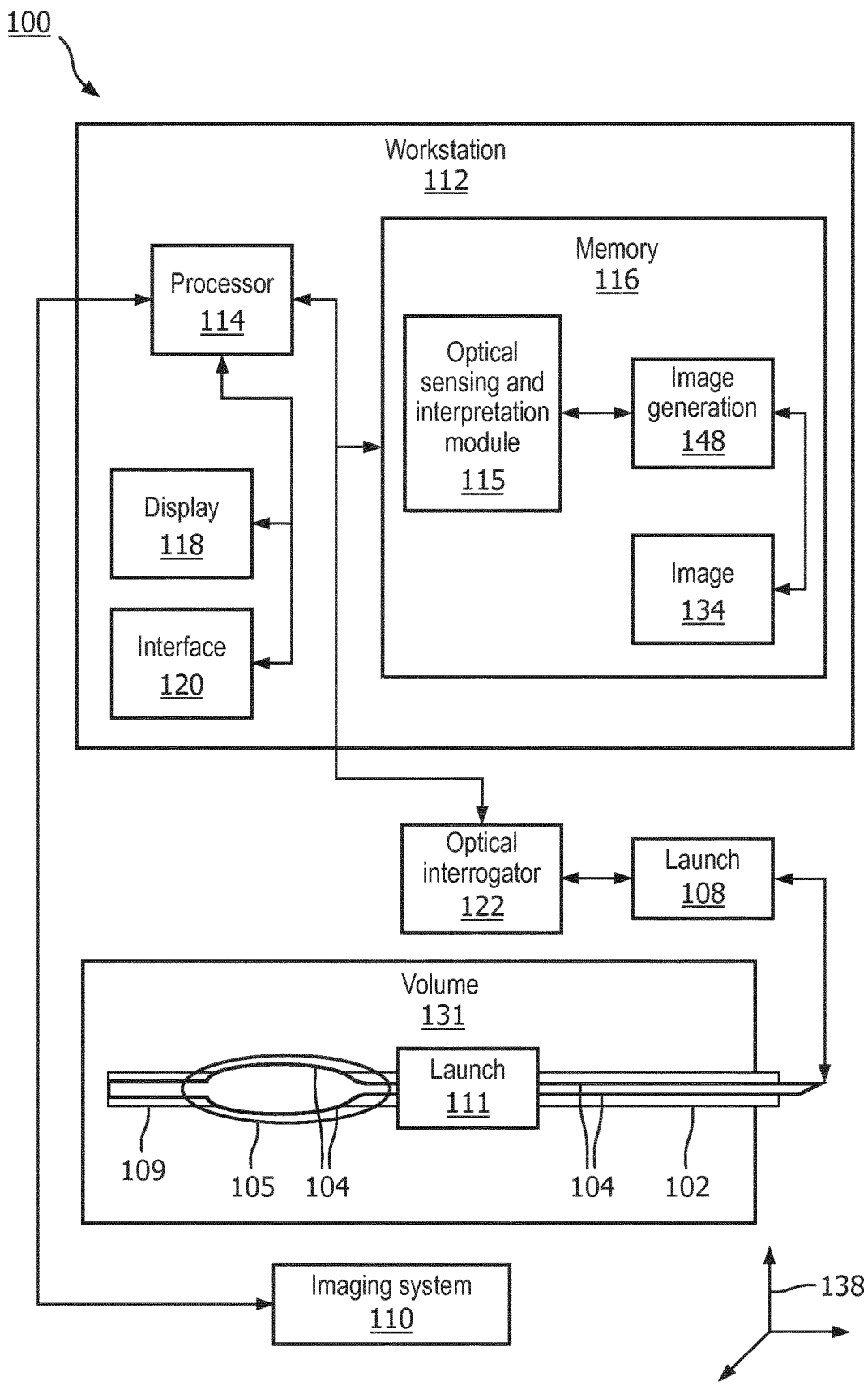
FIG. 6 is a block diagram showing a system for integrating and using multiple shape sensing fibers for monitoring a device or devices in accordance with an illustrative embodiment.

Referring to FIG. 6, a system 100 for integrating and using multiple shape sensing fibers for monitoring a device or devices is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing module or interpreter 115 configured to interpret optical feedback signals from one or more shape or strain sensing optical fibers 104. Optical sensing module 115 is configured to use the optical signal feedback (and any other feedback) to reconstruct deformations, deflections and other changes associated with a medical device or instrument 102 and/or its surrounding region. The medical device 102 may include a catheter, a guidewire, a probe, an endoscope, a robot, an electrode, a filter device, a balloon device, or other medical component, etc.

The fibers 104 on device 102 include one or more optical fibers which are coupled to the device 102 in a set pattern or patterns through an optical interrogator or data acquisition box 122 for the fiber 104. The optical interrogator 122 generates and digitizes all kinds of signals including optical signals to and from the fibers 104. The optical interrogator 122 is connected to the workstation 112, which processes the digitized signals using optical sensing module 115. A launch position 108 is located along the optical fibers 104 and provides a reference position.

The fibers 104 may employ fiber optic Bragg grating sensors, Raleigh scattering or combinations thereof. In some embodiments, Raleigh, Raman, Brillouin or fluorescence scattering may be employed. Rayleigh scatter in standard single-mode communications fiber may be employed. Rayleigh scatter occurs as a result of random fluctuations of the index of refraction in the fiber core. These random fluctuations can be modeled as a Bragg grating with a random variation of amplitude and phase along the grating length.

By using this effect within a length of multi-core fiber, the 3D shape and dynamics of the surface of interest can be followed.

In one embodiment, workstation 112 includes an image generation module 148 configured to receive feedback from the fibers 104 and record shape or strain data as to where the fiber or fibers 104 are located in a volume 131. An image 134 of the fiber(s) 104 within the space or volume 131 can be displayed on a display device 118. The image 134 or images 134 may be captured using an imaging system 110. Imaging system 110 may include an ultrasound system, an x-ray system, an MRI system, a CT system, etc.

Workstation 112 includes the display 118 for viewing internal images of a subject (patient) or volume 131 and may include the image 134 as an overlay or other rendering of the fibers 104 and device 102. Display 118 may also permit a user to interact with the workstation 112 and its components and functions, or any other element within the system 100. This is further facilitated by an interface 120 which may include a keyboard, mouse, a joystick, a haptic device, or any other peripheral or control to permit user feedback from and interaction with the workstation 112.

The fibers 104 may include multiple sensors (fibers) integrated in the device 102 for reconstructing the surface of a balloon or other portion 105 of the device 102. In one embodiment, all sensors 104 reconstruct a full length of the device (from a fixed launch position 108 or to a common coordinate system 138) to a tip 109 of the device 102. In an alternative embodiment, a principal fiber (104) reconstructs the full length of the device 102, while the other fibers reconstruct only a portion of the fiber that covers the balloon or other portion 105. The fibers are registered together to a common coordinate system 138 in a region proximal to the balloon or other portion 105, for example, a second launch position 111 (optional) at or near the balloon or other portion 105.

Figure 7:
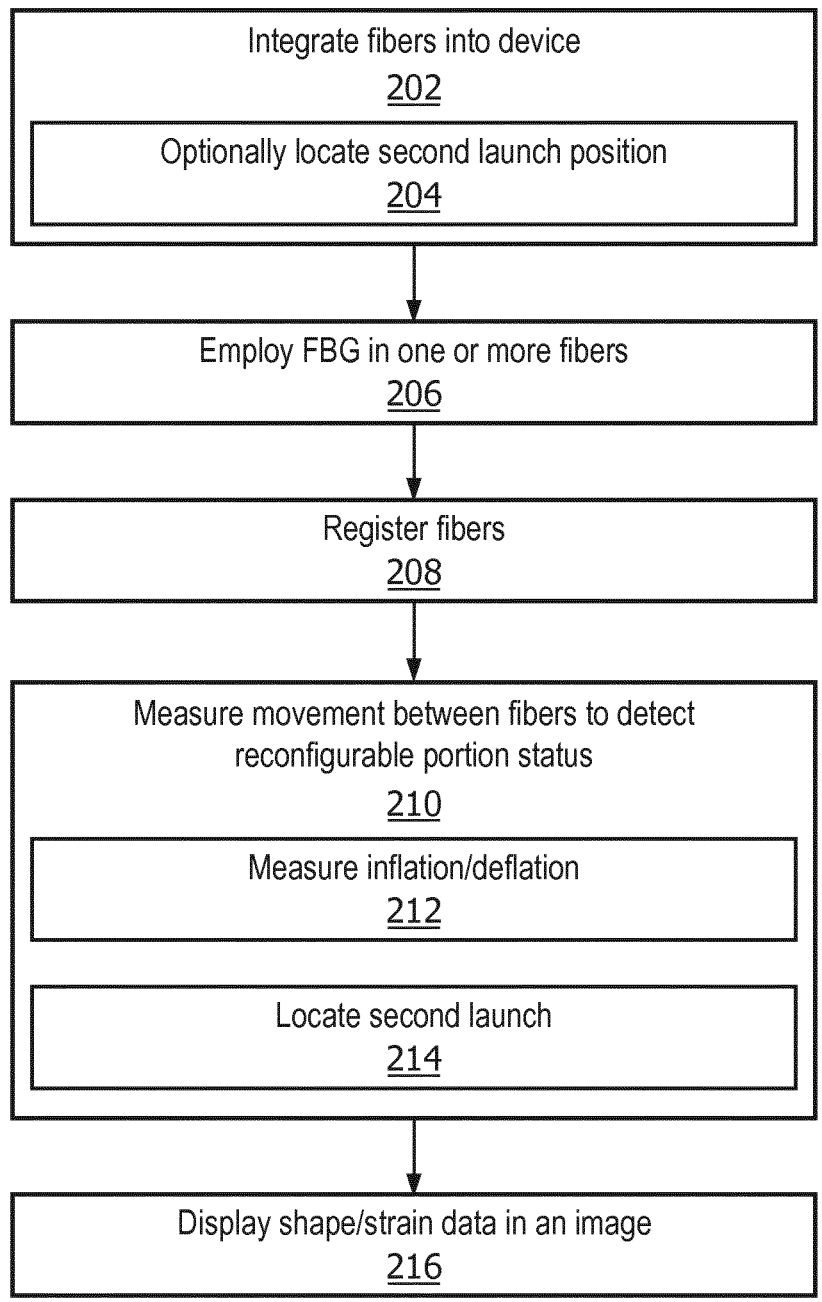
FIG. 7 is a flow diagram showing a method for integrating and using multiple shape sensing fibers for monitoring a device or devices in accordance with an illustrative embodiment.

Referring to FIG. 7, a method for sensing flexure in a reconfigurable portion of a flexible instrument is illustratively shown. In block 202, a plurality of shape or strain sensing optical fibers is configured or integrated in a flexible instrument within at least one lumen. The plurality of optical fibers extends a length of the flexible instrument. In one embodiment, the fibers are fed into a same lumen. In another embodiment, separate lumens are provided for each fiber. The configuration of the fibers may be performed initially to ensure a known relative starting position between the fibers (e.g., setting a size or configuration of the instrument prior to or during deployment). The fibers may be integrated within the device by the manufacturer or may be reconfigured and integrated as needed by the user.

In one embodiment, the plurality of optical fibers may include a principal fiber to measure an entire length of the flexible instrument and at least one supplemental optical fiber to measure the reconfigurable portion of the flexible instrument. The at least one supplemental optical fiber may include a plurality supplemental optical fibers and have a second launch position for the plurality of supplemental optical fibers at or near the reconfigurable portion of the flexible instrument. The second launch position may include a shape to determine a position of the second launch position in an image. In block 204, the second launch position, if employed, is located in an image to remove redundant strain/shape data for the plurality supplemental optical fibers. In block 206, the at least one supplemental optical fiber may include at least one FBG.

In block 208, coordinate systems of each of the plurality of optical fibers may be registered. This is useful especially for fibers with different launch positions. Registration may be made using know techniques.

In some embodiments, its envisioned and preferred that blocks 202, 204, 206, and 208 are performed by a manufacturer during the fabrication of the instrument. However, some or all of these activities of blocks 202, 204, 206, and 208 may be performed by a user.

In block 210, movement is measured for the plurality of optical fibers relative to one another to sense a change in distance between the plurality of optical fibers to detect a state of a reconfigurable portion of the flexible instrument. The flexible instrument may include a balloon catheter, and the reconfigurable portion may include a balloon or balloon portion. In block 212, movement measurements may include measuring the inflation or deflation of the balloon, the expansion/contraction of a stent or endograft, etc. Other devices types may also be employed. In block 214, a second launch position may be employed that includes a shape to determine a position of the second launch position in an image. The second launch position is located in an image to remove redundant strain/shape data for the plurality supplemental optical fibers.

In block 216, the reconfigurable portion of the flexible instrument may be displayed using the strain or shape data from the plurality of optical fibers. The procedure may be continued and completely in accordance with the application.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for multi-sensor integration for therapeutic devices (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A sensor device, comprising:
a flexible instrument including at least one lumen and having a reconfigurable portion less than a length of the flexible instrument; and
a plurality of optical fibers integrated in the flexible instrument in the at least one lumen and extending over the length of the flexible instrument, the plurality of optical fibers being configured for measuring movement relative to one another to sense a change in distance between the plurality of optical fibers to detect a state of the reconfigurable portion of the flexible instrument, wherein the plurality of optical fibers comprises:

a principal optical fiber having a first launch position at or near a proximal position of the flexible instrument and configured for measuring a shape of the flexible instrument along the length of the flexible instrument from the first launch position, and at least one supplemental optical fiber having a second launch position at or near the reconfigurable portion of the flexible instrument and configured for measuring a shape of only the reconfigurable portion of the flexible instrument from the second launch position to detect the state of the reconfigurable portion of the flexible instrument.

2. The device as recited in claim 1, wherein the flexible instrument includes a balloon catheter and the reconfigurable portion includes a balloon.

3. The device as recited in claim 1, wherein the at least one lumen includes a lumen associated with each of the plurality of optical fibers.

4. The device as recited in claim 1, wherein the plurality of optical fibers have registered to a common coordinate system.

5. The device as recited in claim 1, wherein the second launch position includes an identifiable shape to enable determination of a position of the second launch position in an image.

6. The device as recited in claim 1, wherein the at least one supplemental optical fiber includes at least one fiber Bragg grating.

7. A method for sensing flexure in a reconfigurable portion of a flexible instrument, the reconfigurable portion being less than a length of the flexible instrument, the method comprising:

configuring a plurality of shape sensing optical fibers within at least one lumen of the flexible instrument, the plurality of optical fibers extending a length of the flexible instrument, wherein the plurality of optical fibers comprises a principal optical fiber having a first launch position at or near a proximal position of the flexible instrument and at least one supplemental optical fiber having a second launch position at or near the reconfigurable portion of the flexible instrument;

measuring a shape of the flexible instrument along the length of the flexible instrument from the first launch position using the principal fiber; and measuring movement of the plurality of optical fibers relative to one another to sense a change in distance between the plurality of optical fibers by measuring a shape of only the reconfigurable portion of the flexible instrument from the second launch position using the at least one supplemental optical fiber to detect a state of the reconfigurable portion of the flexible instrument.

8. The method as recited in claim 7, wherein the flexible instrument includes a balloon catheter and the reconfigurable portion includes a balloon, and detecting the state of the reconfiguration portion includes detecting inflation or deflation of the balloon.

9. The method as recited in claim 7, further comprising registering coordinate systems of each of the plurality of optical fibers.

10. The method as recited in claim 7, wherein the second launch position includes an identifiable shape for enabling determination of a position of the second launch position in an image, and wherein the method further comprises locating the second launch position in the image to remove redundant shape data for the at least one supplemental optical fiber.

11. The method as recited in claim 7, further comprising displaying the reconfigurable portion of the flexible instrument using shape data from the plurality of optical fibers.

12. A system comprising:

a sensor device comprising a plurality of shape sensing optical fibers integrated in at least one lumen of a flexible instrument and extending over a length of the flexible instrument, the plurality of optical fibers being configured for measuring movement relative to one another to sense a change in distance between the plurality of optical fibers to detect a state of a reconfigurable portion of the flexible instrument that is less than the length of the flexible instrument, wherein the plurality of optical fibers comprises:

a principal optical fiber having a first launch position at or near a proximal position of the flexible instrument and configured for measuring a shape of the flexible instrument along the length of the flexible instrument from the first launch position, and at least one supplemental optical fiber having a second launch position at or near the reconfigurable portion of the flexible instrument and configured for measuring a shape of only the reconfigurable portion of the flexible instrument from the second launch position to detect the state of the reconfigurable portion of the flexible instrument; and an optical interpreter configured to interpret digitized optical signals from the principal optical fiber to reconstruct the shape along the length of the flexible instrument and to interpret digitized optical signals from the at least one supplemental optical fiber to reconstruct only the shape of the reconfigurable portion of the flexible instrument.

13. The system of claim 12, wherein the flexible instrument includes a balloon catheter and the reconfigurable portion includes a balloon.

14. The system of claim 12, wherein the at least one lumen includes a lumen associated with each of the plurality of optical fibers.

15. The system of claim 12, wherein the plurality of optical fibers have registered to a common coordinate system.

16. The system of claim 12, wherein the second launch position includes an identifiable shape to enable determination of a position of the second launch position in an image.

17. The system of claim 12, wherein the at least one supplemental optical fiber includes at least one fiber Bragg grating.

18. The system of claim 12, further comprising:

an optical interrogator configured to generate optical signals provided to the plurality of optical fibers, and to provide the digitized optical signals from the principal optical fiber and the digitized optical signals from the at least one supplemental optical fiber.

* * * * *